United States Patent [19]

Rubin et al.

[11] Patent Number: 4,770,995

[45] Date of Patent: Sep. 13, 1988

[54] DETECTION OF THE SENSITIVITY OF CELLS TO THE EFFECTS OF TUMOR NECROSIS FACTOR AND LYMPHOTOXIN

[75] Inventors: Berish Y. Rubin, Brooklyn; Sylvia L. Anderson, New York; Susan A. Sullivan, Brooklyn; Lloyd J. Old, New York, all of N.Y.; Barbara D. Williamson, Old Greenwich, Conn.; Elizabeth C. Richards, Tarrytown, N.Y.

[73] Assignees: New York Blood Center, Inc; Sloan-Kettering Institute for Cancer Research, both of New York, N.Y.

[21] Appl. No.: 770,804

[22] Filed: Aug. 29, 1985

[51] Int. Cl.[4] .................. G01N 53/00; G01N 33/566; G01N 33/532; G01N 33/534
[52] U.S. Cl. ........................................ 435/7; 436/501; 436/544; 436/545; 436/546
[58] Field of Search .................. 435/7; 436/544, 545, 436/546, 501

[56] References Cited

U.S. PATENT DOCUMENTS

| | | | |
|---|---|---|---|
| 4,309,418 | 1/1982 | Green | 435/68 |
| 4,447,355 | 5/1984 | Sakamoto et al. | 435/68 |
| 4,495,282 | 1/1984 | Ohnishi et al. | 435/68 |

OTHER PUBLICATIONS

J. Cell Biology, 79, 67 (1978) to Green et al.
Cancer Letters, 6, 235–240, (1979) to Green et al.
Cancer Letters, 11, 345–350 (1981) to Green et al.
Williams et al, J. Immunology, 130, 518–520 (1983).
AACR Abstracts, p. 211, No. 831, (1983) to Khan et al.
E. A. Carswell et al, Proc. Natl. Acad. Sci. USA, 72, 3666–3670, (1975).
L. Helson et al, Nature (London) 258, 731–732 (1975).
D. N. Mannel et al, Infect. Immun., 28, 204–211 (1980).
F. C. Kull and P. Cuatrecasas, J. Immunol., 126, 1279–1283 (1981).
N. Matthews and J. F. Watkins, Br. J. Cancer, 38, 302–309 (1978).
J. M. Ostrove and G. E. Gifford, Proc. Soc. Exp. Biol. Med., 160, 354–358 (1979).
S. Green et al, Proc. Natl. Acad. Sci. USA 73, 381–385 (1976).
N. Matthews et al. Br. J. Cancer, 42, 416–422 (1980).
M. R. Ruff and G. E. Gifford, J. Immunol., 125, 1671–1677 (1980).
N. Matthews, Br. J. Cancer, 38, 310–315 (1978).
D. N. Mannel et al, Infect. Immun., 30, 523–530 (1980).
B. D. Williamson et al, Proc. Natl. Acad. Sci. USA, 80, 5397–5401.
Baglioni et al., J. Biol. Chem., 260(25):13395–11397, Nov. 5, 1985.
Hass et al., J. Biol. Chem., 260(22):12214–12218, Oct. 5, 1985.
Kull, Jr. et al., Proc. Nat'l cad. Sci. U.S.A., 82(17):5756–5760 (1985).
Tsujimoto et al., Proc. Nat'l Acad. Sci. U.S.A., 82(22):7626–7630 (1985).
Rubin et al., J. Exp. Med., 162:1099–1104 (1985).
K. Haranaka and N. Satomi, Jpn. J. Exp. Med., 51, 191–194 (1981).

Primary Examiner—Esther M. Kepplinger
Assistant Examiner—Shawn P. Foley
Attorney, Agent, or Firm—Sprung Horn Kramer & Woods

[57] ABSTRACT

A process for predicting the sensitivity of cells, e.g., tumor cells, to the effects of tumor necrosis factor or lymphotoxin involving ascertaining the binding of the tumor necrosis factor or lymphotoxin to the cells, i.e., measuring the number of receptors on the cells.

13 Claims, 5 Drawing Sheets

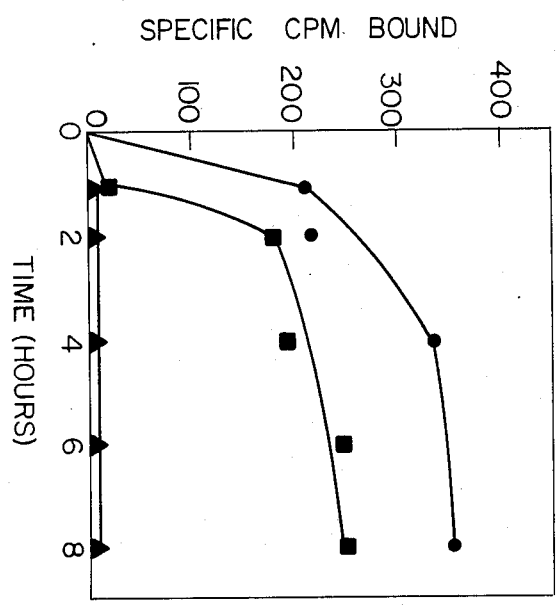
FIG. IA
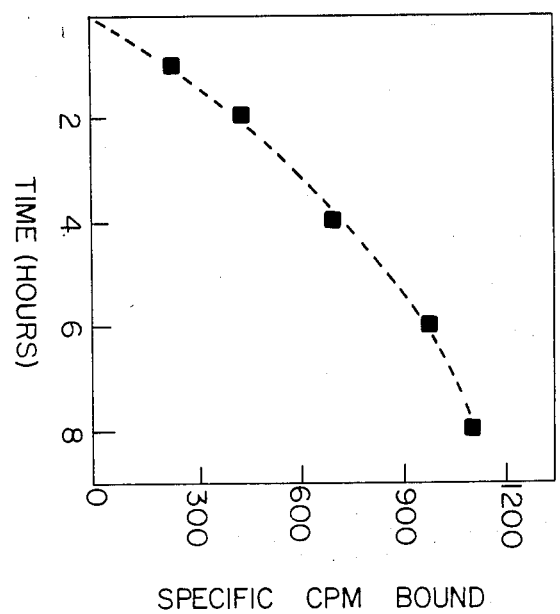
FIG. IB

DETECTION OF THE SENSITIVITY OF CELLS TO THE EFFECTS OF TUMOR NECROSIS FACTOR AND LYMPHOTOXIN

BACKGROUND OF THE INVENTION

The present invention concerns processes for the detection of the sensitivity of cells, e.g., tumor tissues, to the effects of human tumor necrosis factor (TNF) or lymphotoxin (LT). More particularly, the present invention concerns determining the sensitivity of cells, such as tumor cells, to the effects of TNF or LT by measuring the number of receptors on cells.

Hereinafter when TNF or LT are mentioned, applicants are describing molecules that are cytotoxic to cells and cause necrosis of tumors in mice.

Tumor necrosis factor (TNF) was observed by E. A. Carswell et al., *Proc. Natl. Acad. Sci. USA*, 72, 3666–3670 (1975) during a study of the antitumor activity of sera from mice infected with bacillus Calmette-Guerin (BCG) and subsequently injected with endotoxin. These sera have been observed to cause the hemorrhagic necrosis and regression of certain mouse tumors in vivo. These sera were also found to have cytotoxic/cytostatic effects on mouse and human tumor cells in vitro (E. A. Carswell et al, supra; L. Helson et al, *Nature (London)*, 258, 731–732 (1975); D. N. Mannel et al, *Infect. Immun.*, 28, 204–211 (1980); F. C. Kull and P. Cuatrecasas, *J. Immunol.*, 126, 1279–1283 (1981); K. Haranaka and N. Satomi, *Jpn. J. Exp. Med.*, 51, 191–194 (1981)). A similar factor was found to be induced in rats (Carswell et al, supra) and rabbits (Carswell et al, supra, N. Matthews, and J. F. Watkins, *Br. J. Cancer*, 38, 302–309 (1978)); J. Ostrove and G. E. Gifford, *Proc. Soc. Exp. Biol. Medl*, 160, 354–358 (1979)).

The factor present in the sera of animals sensitized to BCG, or other immunopotentiating agents, such as *Corynebacterium parvum* or Zymosan, and then challenged with endotoxin that is capable of causing hemorrhagic necrosis of tumors in vivo has been termed tumor necrosis factor (TNF).

Biochemical characterization has shown that mouse serum TNF exists in at least two forms: a 150,000 $M_r$ form, (Kull and Cuatrecasas, supra and S. Green et al, *Proc. Natl. Acad. Sci USA*, 73, 381–385 (1976)) and a 40,000–60,000 $M_r$ form, D. N. Mannel et al, supra, Kull and Cuatrecasas, supra, and Haranaka, supra. TNF in rabbit serum has been reported to have a molecular weight of 39,000, N. Matthews et al, *Br. J. Cancer*, 42, 416–422 (1980) and 67,000 (M. R. Ruff and G. E. Gifford, *J. Immunol.*, 125, 1671–1677 (1980)).

Studies have indicated that both in vivo and in vitro activities of mouse TNF appear to be a property of the same molecule. The cellular source of TNF in the mouse was initially assumed to be the macrophage, because the agents used to prime for TNF production cause massive hyperplasia of macrophages in liver and spleen, (Carswell et al, supra). From studies of macrophage-rich cell populations in vitro, N. Matthews, *Br. J. Cancer*, 38, 310–315 (1978) and D. N. Mannel et al, supra, a similar conclusion was reached with regard to the source of mouse and rabbit TNF. Direct evidence that macrophages are at least one cell type in the mouse capable of producing TNF comes from studies with cloned lines of mouse histiocytomas. These cells constitutively produce low levels of TNF that are greatly increased after exposure to endotoxin.

B. D Williamson et al, *Proc. Natl. Acad. Sci. USA*, 80, 5397–5401 (1983), described the capacity of human cell lines of hematopoietic origin to produce a factor with TNF activity. Evidence demonstrating that the molecule is a human TNF included the following: (1) the anticellular responses of a panel of human cell lines to human TNF, e.g., TNF(LuKII), or mouse TNF are indistinguishable and can be potentiated in a synergistic fashion by interferon, (2) mouse L cells made resistant to mouse TNF are resistant to human TNF, e.g., TNF(LuKII), (3) mouse L cells made resistant to human TNF, e.g., TNF(LuKII), are resistant to mouse TNF, and (4) human TNF, e.g., TNF(LukII) causes hemorrhagic necrosis of meth A sarcoma in the standard in vivo TNF assay.

Human tumor necrosis factor (TNF) produced by the LuKII cell line has been purified to a specific activity of $1.5 \times 10^7$ units/mg of protein. Examination of this material by sodium dodecyl sulphate polyacrylamide gel electrophoresis demonstrates the presence of seven protein bands with molecular weights ranging from 80,000 daltons to 19,000 daltons. Peptide mapping analysis, as well as studies using monoclonal antibodies to human TNF, have demonstrated that all of the proteins present in these TNF preparations are related.

Heretofore there was no rapid in vitro method to predict whether a tumor will be capable of responding to TNF and LT.

SUMMARY OF THE INVENTION

It is an object of the present invention to determine the sensitivity of cells, e.g., tumor cells, macrophages, B-cells, T-cells, fibroblast cells, epidermal cells and the like, to the effects of TNF or LT.

This and other objects are provided by the present invention wherein a process is provided for determining the sensitivity of cells, e.g., tumor cells, to the effects of TNF or LT.

The present invention concerns predicting the sensitivity of cells, e.g., tumor cells, to TNF by measuring the ability of cells, e.g., tumor cells, to bind to TNF and LT or to bind antibodies directed against the TNF or LT receptors. Cell lines which are capable of binding these factors may be growth inhibited by these factors.

The present invention concerns a further process for predicting the sensitivity of tumor cells to the effects of TNF or LT comprising:

a. contacting (incubating) tumor cells, e.g., disaggregated tumor tissue with TNF or lymphotoxin containing a marker substance, e.g., a radioactive moiety, such as $I^{125}$, $I^{131}$, $C^{14}$ and $H^3$; an enzyme; a fluorescent moiety or a dyestuff, and b. ascertaining if the TNF or lymphotoxin containing the marker substance specifically binds to the tumor cells, i.e., binds via a receptor.

The present invention concerns another process for predicting the sensitivity of tumor cells to the effect of TNF or LT comprising:

a. incubating a first portion of said tumor cells with TNF or lymphotoxin containing a marker substance, b. incubating a second portion of said tumor cells with TNF or lymphotoxin and with TNF or lymphotoxin containing said marker substance, and c. harvesting the tumor cells from step a, d. determining the amount of marker substance on said harvested cells from step c, e. harvesting said tumor cells from step b, f. determining the amount of marker substance on the harvested cells from step e, and g. comparing the amounts from steps d and f.

The present invention concerns still another process for predicting the sensitivity of tumor cells to the effects of TNF and LT comprising incubating tumor cells with a specific antibody to TNF receptor or LT receptor, said antibody containing a marker substance, harvesting the cells and determining the amount of marker on the harvested cells.

DESCRIPTION OF THE DRAWINGS

FIG. 1 shows two graphs, namely, FIG. 1A and FIG. 1B depicting the time course of $^{125}I$ - TNF binding to cells. L(M) (■—■), L(M) resistant to TNF(LukII) (▲—▲) and HeLa cells (●—●) seeded as described herein were incubated for increasing lengths of time in the presence of either 75 units per mL of $^{125}I$—labeled TNF or 75 units per mL of $^{125}I$ labeled TNF plus 1875 units per mL of non-radioactive TNF. Following the time intervals indicated, the cells were harvested and the specific binding of the radiolabeled TNF was determined by subtracting the amount of radioactivity bound in the presence of the excess of non-radioactive TNF from the amount bound in the presence of the $^{125}I$ labeled TNF alone. The time kinetics of binding were performed at 4° C. (FIG. 1A) for the L(M), L(M) resistant to TNF(LukII) and HeLa cells, and at 37° C. (FIG. 1B) for the L(M) cell line.

DETAILED DESCRIPTION OF THE INVENTION

Figure 2A:
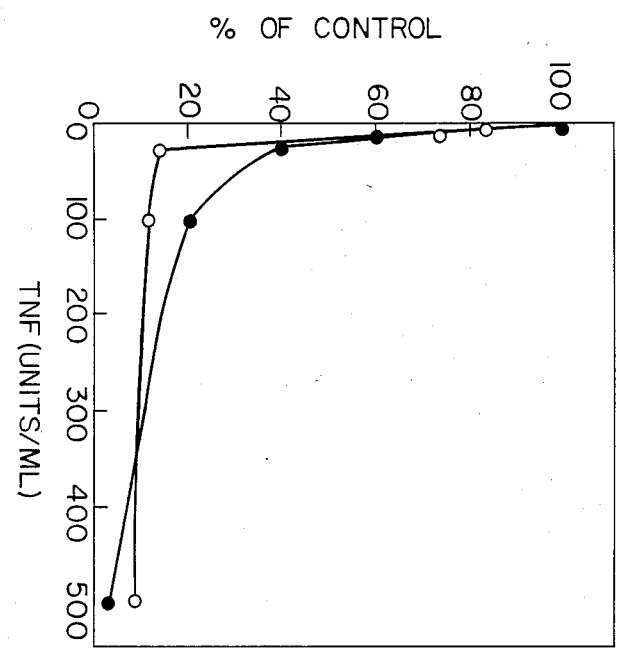
FIG. 2 depicts two plots, namely, FIG. 2A for L(M) cells and FIG. 2B for HeLa cells, showing the competition of binding of $^{125}I$ - TNF by human TNF(LukII) and mouse TNF. L(M) cells (FIG. 2A) and HeLa cells (FIG. 2B) seeded as described herein were incubated for four hours with either 75 units per mL of $^{125}I$ - TNF(LukII) alone (control) or with 75 units/ml of $^{125}I$ - TNF(LukII), and increasing amounts of non-labelled TNF(LukII) (●—●) or mouse TNF (○—○). All values were expressed as a percentage of the $^{125}I$ TNF(LukII) bound in the absence of non-labelled TNF.

Applicants have discovered that radiolabeled human tumor necrosis factor (TNF), e.g., purified $^{125}I$ - labeled TNF(LukII) binds specifically to saturable high affinity receptors, present on cell lines, e.g., human and mouse cell lines sensitive to the cytotoxic effect of human TNF, but not to cell lines resistant to the cytotoxic effect of TNF(LukII) (which are believed to lack receptors to TNF).

Without wishing to be bound by any particular theory of operability, applicants believe that there is a correlation between the presence of receptors and the sensitivity of cells to the cytotoxic effect of TNF and that a mechanism of resistance to TNF may be at the level of the receptor.

Human as well as mouse TNF has been found by applicants to be capable of competing with radiolabeled TNF(LukII) for receptor binding.

An assay according to the present invention involves obtaining a tumor tissue, mechanically disaggregating it and treating it with radiolabeled TNF or LT, both in the absence and presence of an excess of the appropriate nonradioactive lymphokine. If the cells are capable of specifically binding TNF or LT, the amount of radioactivity associated with the cells will be greater in the sample which contained only radiolabeled TNF or LT than in the sample which contained the nonradioactive as well as the radioactive TNF or LT.

The detection of the sensitivity of tumor tissue to the effects of human tumor necrosis factor (TNF) and lymphotoxin (LT) according to the present invention will enable clinicians to judge whether or not a patient should be treated with these agents, much like antibiotic sensitivity screening is performed today. Tests according to the present invention would allow clinicians to predict whether or not a particular tumor would respond to TNF or LT and thus whether that patient would benefit from treatment with these lymphokines.

Non-limiting examples of enzymes that can be used as marker substances in the present invention include beta-lactamase, catalase, beta-glucuronidase, beta-D-glucosidase, peroxidase, urease, glucose, oxidase, alkaline phosphatase and horseradish peroxidase.

When a radioactive moiety is used as a marker substance according to the present invention, its presence can be measured by conventional means such as by using a beta counter, gamma counter or by autoradiography.

When an enzyme is used as a marker substance according to the present invention, its presence can be measured by conventional means, such as by determining enzymatic activity using ELISA techniques.

The invention will now be described with reference to the following non-limiting examples.

EXAMPLES

SUMMARY OF THE EXAMPLES

Mouse L(M) cells, as well as HeLa cells, are sensitive to the cytotoxic effects of human TNF and were used in the study of the biological effects of TNF(LukII). Two sublines of the mouse L(M) cell line resistant to the cytotoxic effects of both human and mouse TNF were developed. One of these lines was selected by growing the L(M) cell line in the presence of mouse TNF (L(M)$_r$-mTNF) and the other by growing the L(M) cell line in the presence of human TNF (L(M)$_r$-hTNF).

The time course of binding of human $^{125}$I-labelled TNF to the L(M) and HeLa cell lines at 37° C. and 4° C. were examined. As can be seen in FIG. 1, the specific binding of $^{125}$I-labelled TNF to the L(M) and HeLa cell lines occurs rapidly and reaches a steady state within four hours at 4°. The amount of specific binding of $^{125}$I-labelled TNF was higher at 37° C. than at 4° C. Examination of the time course of binding of $^{125}$I-labelled TNF to the L(M)$_r$-hTNF cell line revealed that even after eight hours of exposure, the cells were unable to specifically bind TNF. To avoid difficulty in the interpretation of results due to the possibility of metabolism of the TNF that could take place at 37° C., all further experiments were performed at 4° C.

Figure 2B:
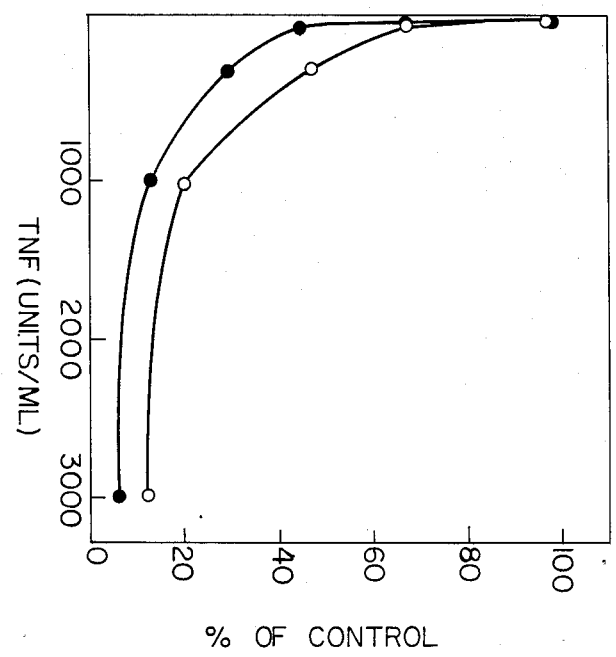

Competition experiments using non-radioactive human and mouse TNF revealed that the binding of $^{125}$I-labelled TNF(LukII) to either the L(M) or HeLa cell lines was competed for by the addition of either non-radioactive TNF(LukII) or non-radioactive mouse TNF (FIG. 2).

Figure 3A:
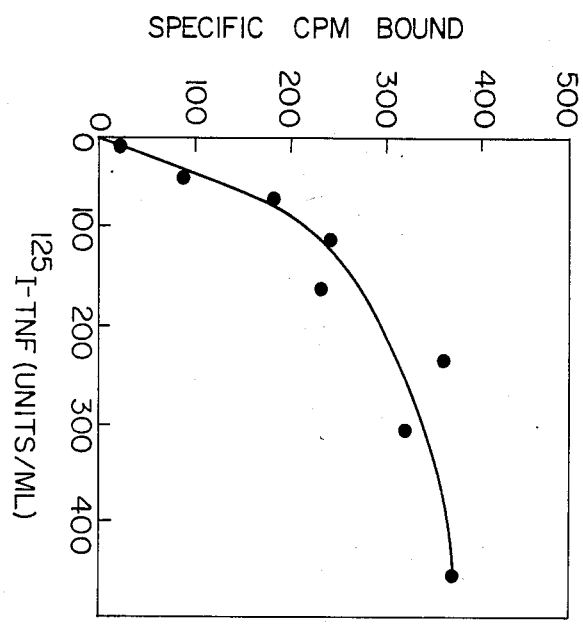
FIG. 3 depicts two plots showing the saturation of $^{125}I$ - TNF(LukII) binding to L(M) cells (FIG. 3A) and HeLa cells (FIG. 3B). L(M) cells and HeLa cells were seeded as described herein. The cells were incubated for five hours with increasing amounts of $^{125}I$ - TNF(LukII), or with increasing amounts of $^{125}I$ - TNF(LukII) and 11,250 units per ml of non-radioactive (non-labelled) TNF(LukII). The cells were then harvested and the specific CPM bound was determined as described hereinabove in regard to FIG. 1.
Figure 3B:
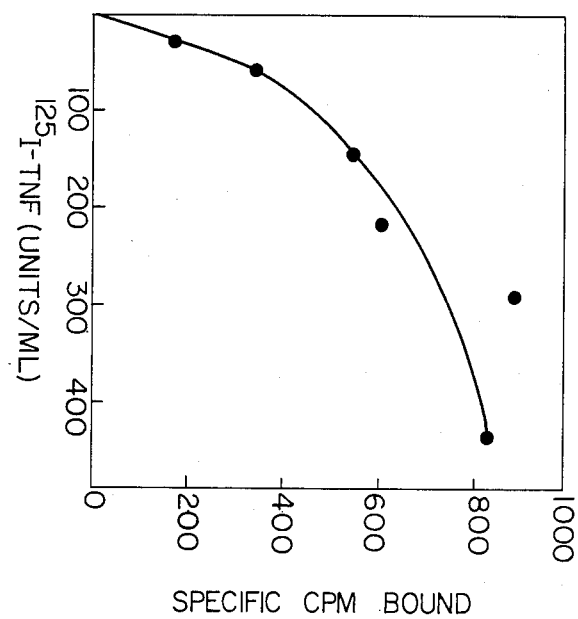
Figure 4A:
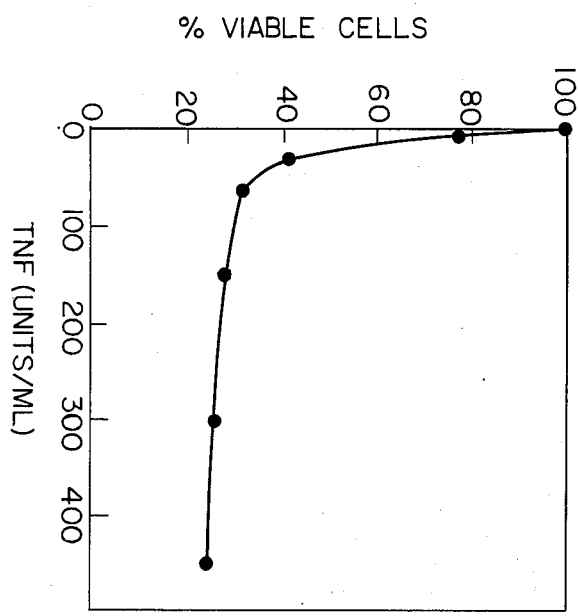
FIG. 4 shows two plots depicting the dose response of cells to the cytotoxic effect of TNF(LukII). L(M) cells (FIG. 4A) seeded at a density of $2 \times 10^6$ cells/25 cm$^3$ flask and HeLa cells (FIG. 4B) seeded at a density of $0.5 \times 10^6$ cells/25 cm$^3$ flask were incubated for 24 hours and 48 hours, respectively. The media was then removed and replaced with media containing increasing concentrations of TNF(LukII). The percentage of viable cells was determined 30 hours later using trypan blue.
Figure 4B:
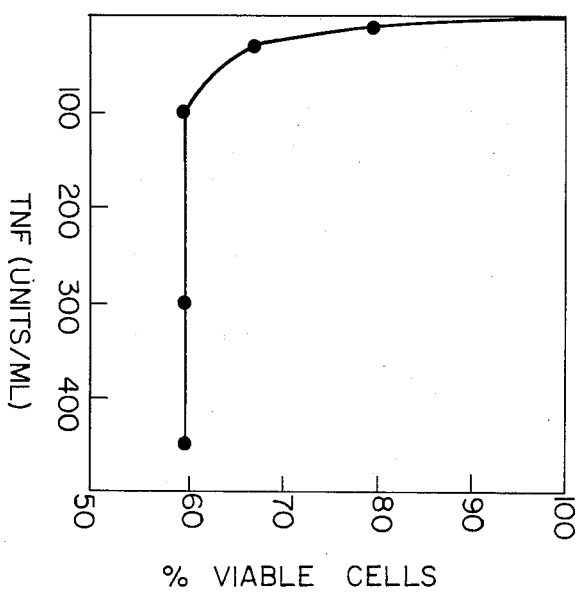
Figure 5A:
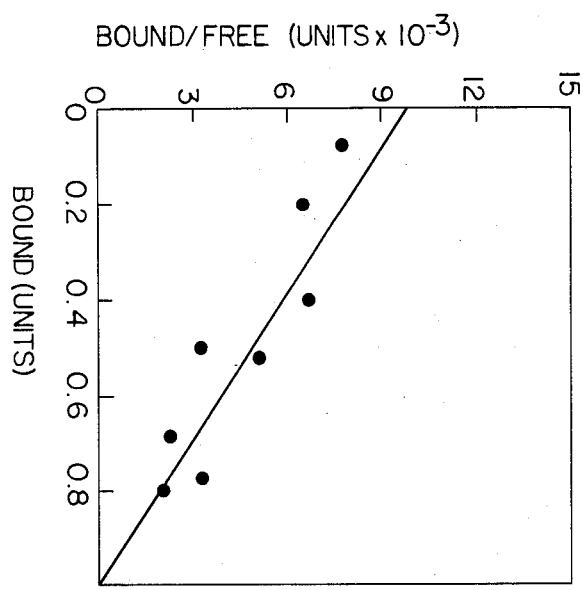
FIG. 5 shows two plots depicting Scatchard analysis of the binding data depicted in FIG. 3. The specific binding results presented in FIG. 3 were converted into Scatchard plots for the L(M) cell line (FIG. 5A) and the HeLa cell line (FIG. 5B).
Figure 5B:
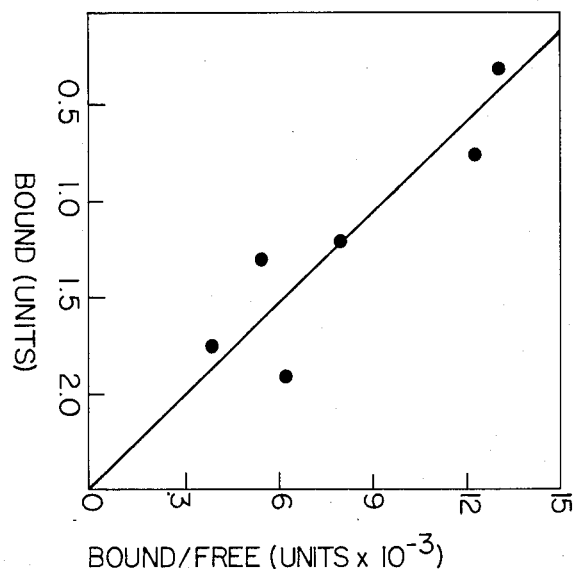

In order to determine whether the binding of TNF(LukII) to the cells was occurring via a receptor, L(M) and HeLa cells were incubated with increasing concentrations of radiolabeled TNF for four hours at 4° C. and the amount of $^{125}$I-labelled TNF associated with the cells was measured. The sites for human TNF on the L(M) and HeLa cell lines were found to be saturable at a TNF concentration of approximately 100 to 150 units/ml (FIG. 3). Examination of the cytotoxic effect of TNF(LukII) on the L(M) and HeLa cell lines (FIG. 4) revealed that the saturation curves of the receptors and the biological dose curves are congruent. Scatchard plots of the data presented in FIG. 3 are shown in FIG. 5. From these results, based on TNF having a molecular weight under nondenaturing conditions of 70,000 and a specific activity of $1.5 \times 10^7$ units/mg of protein, the number of receptors to TNF was calculated to be approximately 200 and 300 for the L(M) and HeLa cell lines, respectively, and the binding constant was calculated to be approximately $1 \times 10^{-10}$M for both L(M) and HeLa cells.

Since Scatchard analysis of the binding data yielded linear plots, it is believed that the TNF binds to homogeneous receptor sites.

EXAMPLE 1

TNF Preparation and Assay

Human TNF(LukII) produced by LukII cells ($8 \times 10^5$ cells/ml in RPMI 1640 media containing 8% fetal calf serum) upon stimulation with 10 ng/ml of mezerein (L.C. Services, Woburn, MA) was purified to a specific activity of $1.5 \times 10^7$ units/mg of protein. The preparation of TNF(LukII) and purified TNF(LukII) are described in a copending application filed on even date herewith and such description is set forth hereinbelow.

Mouse serum TNF was partially purified first on a DEAE column and then on a G-100 Sephadex column to a specific activity of $5 \times 10^4$ units/mg of protein.

The assay for TNF was performed in 96-well microtiter plates. TNF sensitive L(M) cells were added at a density of $2 \times 10^4$ cells/well in 100 uL to equal volumes of serially diluted fractions of TNF sterilized by ultraviolet radiation. After two days at 37° C., the plates were examined by phase-contrast microscopy and the unitage of the sample was calculated as the reciprocal of the highest dilution that killed 50% of the cells. All TNF assays were run in parallel with a TNF(LukII) laboratory standard and all titers were expressed in laboratory units.

A unit of TNF is defined as the amount of protein causing killing of 50% of the cells in the standard in vitro TNF assay.

EXAMPLE 1a

Production of Tumor Necrosis Factor (TNF)

LuKII cells (a cell line of B-cell origin) were obtained as described in L.A. Pickering, L.H. Kronenberg and W.E. Stewart II, Proc. Natl. Acad. Sci USA, 77, 5938–5942 (1980)) and were cultured in the following manner in order to obtain human tumor necrosis factor (hTNF) produced by the LuKII cells:

LuKII cells ($8 \times 10^5$ cells/ml) were placed in RPMI 1640 media containing 8% fetal calf serum with 10 ng/ml of mezerein (L.C. Services, Woburn, MA) for 48 hours. The cells were then removed from the media by centrifugation, resuspended in fresh RPMI 1640 media lacking any protein supplement and allowed to incubate for an additional 48 hours, at which time the cells were removed by centriguation, leaving the supernatant containing TNF(LukII).

EXAMPLE 1b

Purification of TNF(LukII)

TNF(LukII) was purified sequentially using controlled pore glass, lentil lectin Sepharose and procion red agarose column chromatography as follows (all affinity chromatography procedures were carried out at room temperature and all column fractions were collected in polypropylene tubes or bottles):

Culture media of the LukII cell line (8 liters) containing 200 units/mL of TNF activity was applied to a column of controlled pore glass-350 (50 mL) (Electronucleonics, Fairfield, N.J.) equilibrated with phosphate buffered saline (PBS) (20 mM sodium phosphate, pH 7.0, 0.15M NaCl which bound all of the TNF(LukII) activity. The column was washed with the following buffers in sequence: PBS (75 mL), PBS containing 20% ethylene glycol (v/v) (E$_1$) (225 mL), PBS (120 mL), 20 mM sodium phosphate, pH 7.0, containing 1.15M NaCl (PBS+1M NaCl) (E$_2$) (175 mL), PBS (50 mL), 5 mM sodium phosphate, pH 6.8, (E$_3$) (225 mL), and 5 mM sodium phosphate, pH 6.8, containing 5% triethylamine (v/v) (E$_4$) (150 mL). Eluted fractions were collected in polypropylene bottles. The material eluted with the E$_4$ buffer was collected in 50 mL aliquots. 150 mL of the partially purified TNF(LukII) eluted from the controlled pore glass column was then applied to a lentil lectin Sepharose column (10 mL) (Pharmacia, Piscataway, N.J.), equilibrated with PBS, which was then washed first with phosphate buffered saline (PBS) (40 mL) followed by a 0.02M sodium phosphate buffer, pH 6.8, containing 1.15M NaCl (PBS+1M NaCL) (24 mL). The TNF activity was then eluted from this column with PBS+1M NaCl buffer containing 0.2M alpha-methyl-D-mannoside (60 mL). The material eluted with the alpha-methyl-D-mannoside containing buffer was collected in 10 mL aliquots. All of the TNF(LukII) activity bound to the lentil lectin Sepharose column and 39% of the activity was recovered in the alpha-methyl- D-mannoside- containing buffer. The further washing of the column with the above buffer containing 50% ethylene glycol eluted only a small amount of TNF(LukII) activity. The eluted TNF(LukII) (60 mL) was then diluted in half with PBS and loaded onto a procion red agarose column (4 mL) (Bethesda Research Laboratory, Bethesda, Maryland) equilibrated with 20 mM sodium phosphate, pH 6.8, 0.65M NaCl (PBS+0.5M NaCl). The column was washed sequentially with the following buffers: PBS+0.5M NaCl ($E_1$) (30 mL), PBS+1M NaCl ($E_2$) (8 mL), PBS (8 mL), PBS containing 50% ethylene glycol (v/v) ($E_3$) (8 mL), PBS (8 mL) and 0.1M Tris-HCl, pH 9.4+0.1M NaCl ($E_4$) (8 mL), which removed protein having no TNF activity. The column was then washed with 0.1M Tris-HCL, pH 9.4, containing 0.1M arginine (24 mL). The TNF(LukII) activity was eluted with this buffer (in 4 mL aliquots) yielding TNF(LukII) with a specific activity of $1.5 \times 10^7$ units/mg of protein. Table 1 below summarizes the purification scheme for TNF(LukII) with resulting recoveries and specific activities of the resulting fractions.

The labelled protein was then separated from the unbound $^{125}I$ using a P-4 column (Biorad, Richmond, CA) equilibrated with phosphate buffered saline (PBS) containing 50 μg/ml of cytochrome-C. The iodinated material eluted in the void volume of the column in 8 mL was divided into aliquots and stored at $-80°$ C. The iodinated material contained 60,000 units/ml and $7.5 \times 10^9$ CPM/mg of TNF(LukII). The radio-iodination of the TNF(LukII) was carried out without any loss of biological activity.

EXAMPLE 4

Assay for the Binding of $^{125}I$-labelled TNF(LukII) to Cells

L(M) cells and its resistant subclones seeded in 25 cm² flasks at a density of $2 \times 10^6$ cells/flask were allowed to adhere to be flasks for a 24 hour period before being treated with radiolabelled TNF(LukII). At this time, the flasks contained approximately $3.5 \times 10^6$ cells/flask. HeLa cells seeded in 25 cm² flasks at a density of

TABLE I

| Column | Purification of TNF (LukII) | | | | | |
|---|---|---|---|---|---|---|
| | Load (units) | Load (Specific Activity) μ/mg | Recovery (units) | Recovery (Specific Activity) μ/mg | % Recovery | Fold Purification |
| Controlled Pore Glass | $1.6 \times 10^6$ | $5.3 \times 10^3$ | $9.6 \times 10^5$ | $3.8 \times 10^5$ | 60% | 72X |
| Lentil Lectin Sepharose | $9.6 \times 10^5$ | $3.8 \times 10^5$ | $6.3 \times 10^5$ | $1.3 \times 10^6$ | 39% | 245X |
| Procion Red Agarose | $6.3 \times 10^5$ | $1 \times 10^6$ | $6.3 \times 10^5$ | $1.5 \times 10^7$ | 39% | 2830X |

EXAMPLE 2

Preparation of Monoclonal Antibodies to the Receptors for Human TNF or Human Lymhotoxin BALB/c mice can be injected with receptors for purified human TNF or human lymphotoxin. For the initial injection, the receptors can be mixed with Freund's complete adjuvant (1:1) and injected subcutaneously. Subsequent injections can be given intraperitoneally in the absence of adjuvant. Serum antibody to the receptors can be determined by an enzyme linked immunosorbent assay (ELISA) in which the receptors can be bound to polystyrene plates. When the mice are hyperimmunized to the receptors, the spleens of the mice can be removed and fused with cells of the $P_3U_1$ mouse plasmacytoma cell line. Resultant clones can be screened for their ability to bind the receptors in ELISA assays. Hybridomas grown in tissue culture media as well as in ascites may serve as a source of antibody to the receptors. If mice fail to develop antibody to the TNF or LT receptor, the preparation of monoclonal antibodies to the receptors will be accomplished by immunizing rats from which monoclonal antibodies can be made.

EXAMPLE 3

Radio-iodination of TNF(LukII)

TNF(LukII) was labelled with $^{125}I$ by using chloramide 1,3,4,6-tetrachloro-3α,6α-diphenylglycoluril (Iodogen, Pierce Chemical Co., Rockford, IL) as follows. Polypropylene tubes were coated with 100 μg of iodogen (dissolved in chloroform) by evaporation of the solvent. A sample of TNF(LukII) (160,000 units/ml in 3 mL) with a specific activity of $1.5 \times 10^7$ units/mg of protein was incubated for 25 minutes at room temperature in an iodo-gen coated tube containing 6 mci of $^{125}I$.

$1.5 \times 10^6$ cells/flask were allowed to adhere to the flasks for a 48 hour interval before being treated with radiolabeled TNF(LukII). At this time, the flasks contained approximately $5 \times 10^6$ cells/flask. $^{125}I$-labelled TNF(LukII) was added to the flasks in one mL of Eagles's minimal essential media (MEM), containing 10% fetal bovine serum (Gibco, Grand Island, NY). Actual amounts of TNF(LukII) and the time intervals employed are as described hereinabove. Following the appropriate incubation period(s), the cells were washed three times with cold PBS, scraped from the flask in PBS and centrifuged at 15,000 x g for 5 minutes over a cushion of PBS containing 5% sucrose. The sucrose cushion was then removed and the cell pellets counted in a gamma radiation counter.

EXAMPLE 5

Measurements of the Cytotoxic Effect of TNF(LukII)

L(M) cells seeded at a density of $2 \times 10^6$ cells/25 cm² flask and HeLa cells seeded at a density of $0.5 \times 10^6$ cells/25 cm² flask were allowed to adhere to the flasks for 24 hours and 48 hours, respectively. The media was then removed from the flasks and was replaced with media containing increasing concentrations of TNF(LukII). The percentage of viable cells was determined 30 hours later using trypan blue.

EXAMPLE 6

Immunofluorescent staining technique for localization of receptors

Approximately six micron thick frozen sections of tumor tissue can be placed on slides and fixed with formaldehyde or another fixative (e.g., glutaraldehyde, acetone and methanol) which does not destroy antigens.

These sections can be incubated for an hour with the monoclonal antibodies (prepared as discussed above in Example 2) directed against the TNF or LT receptor and then washed with PBS. After the drying of the slide, the sections can be incubated for one hour at 37° C. with affinity purified rabbit-anti-mouse (or rabbit-anti-rat) immunoglobulin conjugated with fluorescein isothiocyanate. The slide can then be washed, counterstained with Evan's blue, washed again and covered with 10% glycerol. Examination of the slides can be carried out using a Nikon Optiphot Epifluorescence microscope.

EXAMPLE 7

Immunoperoxidase staining technique for localization of receptors

Frozen sections prepared, fixed and washed as described above can be incubated with 0.3% hydrogen peroxide in PBS for 5 minutes to block endogenous peroxidases. These slides can then be washed and incubated with filtered bovine serum albumin (1% BSA/PBS) for 5 minutes to block nonspecific uptake. The slides can then be washed and incubated for an hour with the monoclonal antibodies directed against the TNF or LT receptor prepared as described above in Example 2 above. Following this incubation period, the cells can be washed with PBS, incubated with bi-otinylated horse-anti-mouse (or rabbit-anti-rat) antibody, washed again with PBS, and then incubated with avidin DH biotinylated horseradish peroxidase H complex. The sections can then be washed with PBS and incubated for 10 minutes with the substrate (0.01% hydrogen peroxide and 0.05% 3,3-diaminobenzidine tetrahydrochloride) for localization of binding. The cells can then be washed in distilled water, counterstained, dehydrated and mounted in fixative for examination.

It will be appreciated that the instant specification and claims are set forth by way of illustration and not limitation, and that various modifications and changes may be made without departure from the spirit and scope of the present invention.

What is claimed:

1. A process for predicting the sensitivity of cells to the effects of tumor necrosis factor or lymphotoxin comprising measuring the number of tumor necrosis factor or lymphotoxin receptors on said cells, the number of said receptors being correlected to the sensitivity of the cells to tumor necrosis factor or lymphotoxin.

2. A process according to claim 1, wherein said cells are tumor cells.

3. A process according to claim 1, wherein said measuring of the number of receptors on said cells is accomplished by:
   a. incubating said cells with tumor necrosis factor or lymphotoxin labeled with a marker substance, and
   b. ascertaining if the labeled tumor necrosis factor or lymphotoxin specifically binds to the cells.

4. A process according to claim 2, wherein said tumor cells are in the form of tumor tissue.

5. A process according to claim 3, wherein said marker substance is selected from the group consisting of a radioactive moiety, an enzyme, a fluorescent moiety and a dyestuff.

6. A process according to claim 3, wherein said marker substance is $I^{125}$.

7. A process according to claim 1, wherein said measuring of the number of receptors on said cells is accomplished by incubating a specific antibody to tumor necrosis factor receptor or lymphotoxin receptor with said cells, said antibody labeled with a marker substance, harvesting said cells and determining the amount of marker on the harvested cells.

8. A process according to claim 7, wherein said marker is selected from the group consisting of a radioactive moiety, an enzyme, a fluorescent moiety and a dyestuff.

9. A process according to claim 7, wherein said marker is $I^{125}$.

10. A process for predicting the sensitivity of tumor cells to the effects of tumor necrosis factor or lymphotoxin comprising:
    a. incubating a first portion of said cells with tumor necrosis factor or lymphotoxin, labeled with a marker substance,
    b. incubating a second portion of said cells with unlabeled tumor necrosis factor or lymphotoxin and with labeled tumor necrosis factor or lymphotoxin, and
    c. harvesting the cells from step a,
    d. determining the amount of marker substance on the harvested cells from step c,
    e. harvesting the cells from step b,
    f. determining the amount of marker substance on the harvested cells from step e, and
    g. comparing the amounts of marker substance on the harvested cells from steps d and f, such that if the amounts from steps d and f are approximately the same, then the cells are not sensitive to TNF or LT.

11. A process according to claim 10, wherein the marker substance is selected from the group consisting of a radioactive moiety, an enyzme, a fluorescent moiety and a dyestuff.

12. A process according to claim 10, wherein said marker substance is $I^{125}$.

13. A process according to claim 10, wherein said tumor cells are in the form of tumor tissue.

* * * * *